(12) United States Patent
Fujita

(10) Patent No.: US 8,233,659 B2
(45) Date of Patent: Jul. 31, 2012

(54) RADIOGRAPHIC APPARATUS

(75) Inventor: Akinori Fujita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 324 days.

(21) Appl. No.: 12/721,247

(22) Filed: Mar. 10, 2010

(65) Prior Publication Data
US 2010/0239145 A1 Sep. 23, 2010

(30) Foreign Application Priority Data
Mar. 17, 2009 (JP) .................. 2009-064097

(51) Int. Cl.
G06K 9/00 (2006.01)
G01N 23/04 (2006.01)
(52) U.S. Cl. .................. 382/100; 382/131; 378/62
(58) Field of Classification Search .................. 382/100, 382/128–132, 181, 254, 275; 378/4, 62, 378/21–24, 207, 205, 56; 250/252.1; 705/2; 128/922
See application file for complete search history.

(56) References Cited

U.S. PATENT DOCUMENTS

| | | | | |
|---|---|---|---|---|
| 4,947,323 A * | 8/1990 | Smith | ................ | 382/132 |
| 6,000,847 A * | 12/1999 | Close et al. | ................ | 378/207 |
| 2006/0011853 A1* | 1/2006 | Spartiotis et al. | ........ | 250/370.13 |
| 2011/0075928 A1* | 3/2011 | Jeong et al. | ................ | 382/181 |

FOREIGN PATENT DOCUMENTS
JP 2002-257939 A 9/2002
* cited by examiner

Primary Examiner — Samir Ahmed
Assistant Examiner — Mehdi Rashidian
(74) Attorney, Agent, or Firm — Cheng Law Group, PLLC

(57) ABSTRACT

A radiographic apparatus includes a radiation source for emitting radiation, a radiation detection device having radiation detecting elements arranged longitudinally and transversely for detecting the radiation, a radiation grid, and an object image correcting device. The object image correcting device generates a corrected image by deriving components of direct radiation in pixel values of an object image from a dark equation specifying that an average of radiation intensity in a dark pixel group formed of a dark pixel showing a shadow of one of absorbing foil strips and adjacent pixels transversely adjoining the dark pixel of each image is a sum of the components of direct radiation and components of indirect radiation, and light equations specifying that an average of radiation intensity in light pixels free of the shadows of the absorbing foil strips is a sum of the components of direct radiation and the components of indirect radiation.

20 Claims, 8 Drawing Sheets

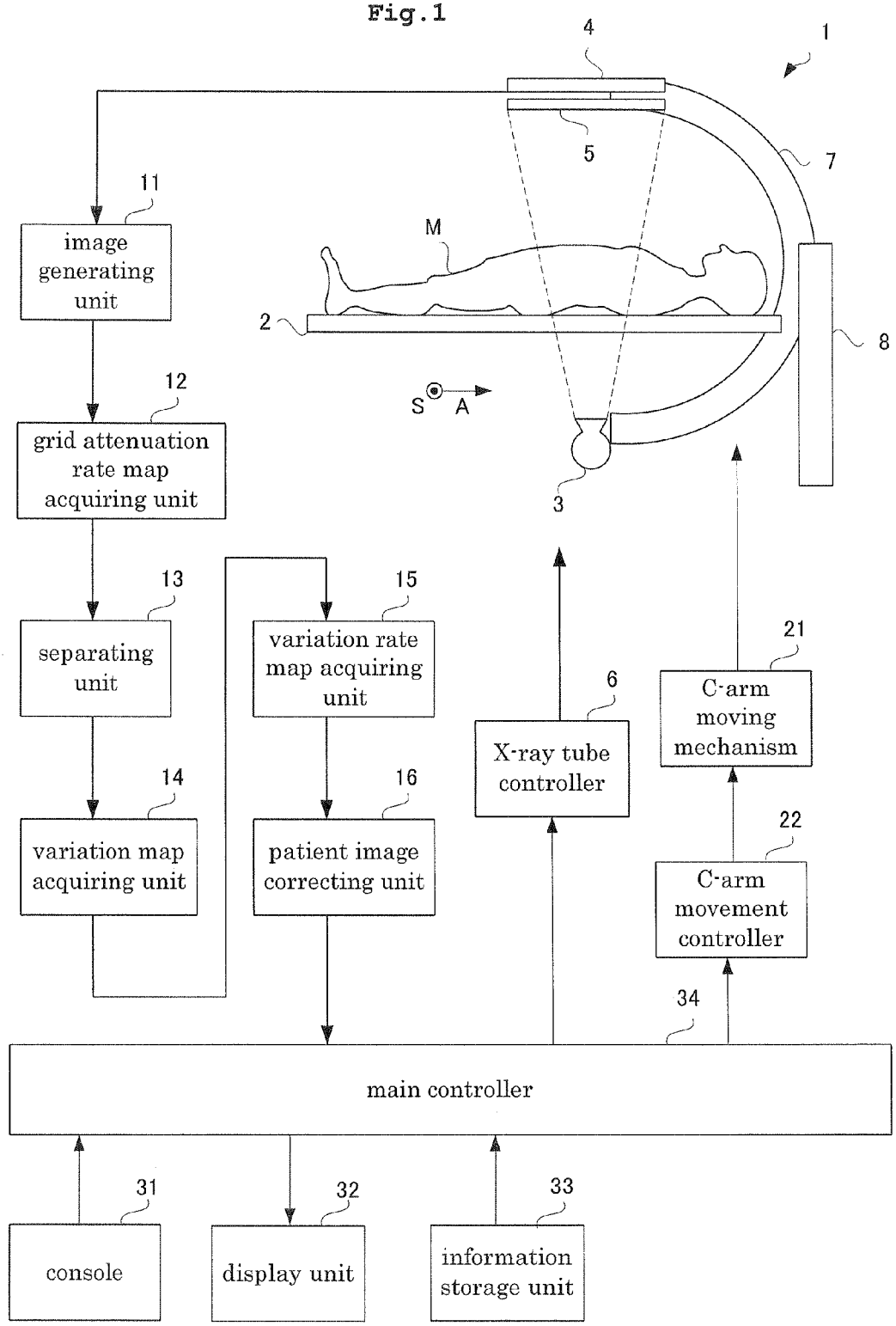

RADIOGRAPHIC APPARATUS

BACKGROUND OF THE INVENTION (1) Field of the Invention

This invention relates to a radiographic apparatus for picking up fluoroscopic images of an object under examination with radiation, and more particularly to a radiographic apparatus having a radiation grid for removing scattered radiation.

(2) Description of the Related Art

Medical institutions have radiographic apparatus installed therein for picking up fluoroscopic images of patients. As shown in FIG. 7, such a radiographic apparatus 51 includes a top board 52 for supporting a patient M, a radiation source 53 for emitting radiation, and a radiation detector 54 for detecting the radiation.

The radiation detector 54 has a radiation grid 55 placed on a radiation incidence plane thereof for removing scattered radiation produced from the patient M. As shown in FIG. 9A, the radiation grid 55 has elongated strips of absorbing foil 55a arranged as in a blind (see Japanese Unexamined Patent Publication No. 2002-257939, for example).

As shown in FIG. 9B, the radiation detector 54 has radiation detecting elements 54a arranged in a two-dimensional matrix form. Falling on this radiation detector 54 are a fluoroscopic image of the patient M as shown in FIG. 8A, and indirect radiation not removed by the radiation grid 55 and shadows of the radiation grid 55 as shown in FIG. 8B. In FIG. 8B, it appears as if the indirect radiation has uniform intensity. Actually, however, the indirect radiation presents a distribution corresponding to positions of the absorbing foil strips 55a.

Components of this indirect radiation are obstructive to generation of the fluoroscopic image of the patient M. So, in recent years, a technique of acquiring fluoroscopic images of the patient M has been developed, which removes the components of indirect radiation from the pixels outputted from the radiation detector 54. When acquiring such a fluoroscopic image, the shadows of the absorbing foil strips 55a falling on the radiation detector 54 pose a problem. As shown in FIG. 9A, shadows S of the absorbing foil strips 55a fall on the radiation detector 54. When seen in plan, as shown in FIG. 9B, there appears a regular arrangement of lines of radiation detecting elements 54a including the shadows S of the absorbing foil strips 55a, and lines of radiation detecting elements 54a free of the shadows S of the absorbing foil strips 55a.

The following method is used to remove components of indirect radiation from an image including the shadows S of the absorbing foil strips 55a. First, a region R of the image is assumed, which consists of a pixel including a shadow (dark pixel a2) and two pixels adjacent thereto and without shadows (light pixels a1 and a3). An equation is formed for each pixel of this region R, indicating that its pixel value is a sum of a component of direct radiation and a component of indirect radiation. Since the three pixels are included in the area R, simultaneous equations consisting of three equations are formed. That is, the following simultaneous equations are formed:

Pixel value of dark pixel $a2$=component of direct radiation+component of indirect radiation Pixel value of light pixel $a1$=component of direct radiation+component of indirect radiation Pixel value of light pixel $a3$=component of direct radiation+component of indirect radiation Components of direct radiation in the region R are obtained by solving these simultaneous equations. This operation may be carried out for the entire area of the image and the image reconstructed, thereby to acquire a fluoroscopic image without influences of the indirect radiation and well suited for diagnosis.

However, the conventional radiographic apparatus has the following drawback.

The conventional radiographic apparatus presupposes that positions of the shadows of the radiation grid 55 are always fixed relative to the radiation detector 54. In practice, however, the positions of the shadows can shift relative to the radiation detector 54 during radiography. In certain radiographic apparatus, the radiation source 53 and radiation detector 54 are revolvable about an axis extending longitudinally of the top board 2. In such radiographic apparatus, when fluoroscopic images are picked up while revolving the radiation source 53 and radiation detector 54, since the radiation source 53 and radiation detector 54 are heavy objects, those revolution distorts the structure supporting the radiation source 53 and radiation detector 54. This will shift a relative position between the radiation source 53 and radiation detector 54.

The above method of solving the simultaneous equations for the region R assumes that the shadow of absorbing foil strip 55a is not included in the light pixels. If the shadow of absorbing foil strip 55a moves to a position bridging the dark pixel and light pixel with revolution of the radiation source 53 and radiation detector 54, it will become impossible to separate the direct radiation from the indirect radiation accurately by the above method.

SUMMARY OF THE INVENTION

This invention has been made having regard to the state of the art noted above, and its object is to provide a radiographic apparatus which can acquire fluoroscopic images well suited for diagnosis even if shadows of a radiation grid move relative to a radiation detector.

The above object is fulfilled, according to this invention, by a radiographic apparatus comprising a radiation source for emitting radiation; a radiation detection device having radiation detecting elements arranged longitudinally and transversely for detecting the radiation; a radiation grid placed to cover a radiation detecting plane of the radiation detecting device, and having absorbing foil strips extending longitudinally and arranged transversely; an image generating device for generating images based on detection signals outputted from the radiation detecting device; an air image storage device for storing an air image generated by air radiography carried out without an object under examination interposed between the radiation source and the radiation detecting device; an object image storage device for storing an object image generated by object radiography carried out with the object under examination interposed between the radiation source and the radiation detecting device; and an object image correcting device for generating a corrected image from components of direct radiation included in the object image and determined based on the air image and the object image; wherein the object image correcting device is arranged to generate the corrected image by deriving the components of direct radiation in pixel values of the object image from a dark equation specifying that an average of radiation intensity in a dark pixel group formed of a dark pixel showing a shadow of one of the absorbing foil strips and adjacent pixels transversely adjoining the dark pixel of each image is a sum of the components of direct radiation and components of indirect radiation, and light equations specifying that an average of radiation intensity in light pixels free of the shadows of the absorbing foil strips is a sum of the components of direct radiation and the components of indirect radiation.

Preferably, the radiographic apparatus further comprises a phantom image storage device for storing a phantom image generated by phantom radiography carried out with a phantom interposed between the radiation source and the radiation detecting device, wherein the object image correcting device is arranged to generate the corrected image based on the phantom image in addition to the air image and the object image.

The radiographic apparatus of this invention is constructed to acquire a corrected image based on the air image, phantom image and object image. The corrected image is acquired only from the components of direct radiation exiting the object. This provides a clear fluoroscopic image with contrast not impaired by indirect radiation. According to this invention, radiography for the phantom image can be omitted.

Moreover, in acquiring the corrected image, the components of direct radiation of the object image are obtained by solving simultaneous equations consisting of the light equations relating to light pixels free of the shadows of the absorbing foil strips, and the dark equation relating to the dark pixel group having the shadow of one of the absorbing foil strips. That is, the components of direct radiation are obtained on an assumption that the shadow of one of the absorbing foil strips is present somewhere in the dark pixel group. Even if the shadows of the absorbing foil strips move relative to the arrangement of radiation detecting elements in the radiation detecting device, the shadow of one of the absorbing foil strips exists in one or more pixels of the dark pixel group. The shadow of the absorbing foil strip never deviates from the dark pixel group. Therefore, the object image correcting device can solve the simultaneous equations reliably, to provide a corrected image well suited for diagnosis.

Preferably, the dark pixel group is formed of three pixels arranged transversely.

In the above construction, the dark pixel group is formed of three pixels. The shadows of the absorbing foil strips can move to an extent corresponding to one pixel transversely of the arrangement of the radiation detecting elements. Therefore, the dark pixel group can be set to cover three pixels. An excessively large dark pixel group would lead to a blurred image. According to the above construction, the number of pixels included in the dark pixel group is a minimum.

Preferably, the object image correcting device is arranged to derive the components of direct radiation in the object image from three simultaneous equations including the dark equation and light equations relating to two light pixels transversely adjoining the dark pixel group.

According to the above construction, the components of direct radiation in the object image are determined by the three simultaneous equations. Such construction can solve the simultaneous equations reliably.

Preferably, the radiographic apparatus further comprises a support for supporting the radiation source and the radiation detecting device; a support moving device for moving the support; and a support movement control device for controlling the support moving device.

The above construction represents one specific embodiment of this invention. That is, the radiation source and the radiation detecting device are movable. This movement includes rotation. Since the radiation source and the radiation detecting device are heavy objects, the support will bend when rotated. This shifts a positional relationship between the radiation source and radiation detecting device slightly (about 2 mm). Then, the shadows of the absorbing foil strips of the radiation grid falling on the radiation detecting device will move an amount correspond to about one detecting element transversely of the radiation detecting device. According to the above construction, even if such a phenomenon occurs, the shadow of the absorbing foil strip will never protrude sideways from the dark pixel group. Therefore, the components of direct radiation of the object image can be obtained reliably.

In the above radiographic apparatus, the support preferably comprises a C-arm.

The above construction represents one specific embodiment of this invention. The C-arm in the above construction is suitable for supporting the radiation source and the radiation detection device while maintaining the positional relationship thereof. However, the C-arm will bend when rotated, under the weight of the radiation source. According to this invention, even if the C-arm bends easily, the components of direct radiation of the object image can be obtained reliably.

In the above radiographic apparatus, the absorbing foil strips of the radiation grid, preferably, are formed of one of a molybdenum alloy and a tantalum alloy which absorbs radiation.

The above construction represents one specific embodiment of this invention. That is, the absorbing foil strips are formed of a molybdenum alloy or a tantalum alloy. Then, the absorbing foil strips can reliably absorb indirect radiation incident thereon.

The radiographic apparatus of this invention is constructed to acquire a corrected image based on an air image and an object image. In acquiring the corrected image, components of direct radiation are obtained by solving simultaneous equations consisting of light equations relating to light pixels free of the shadows of the absorbing foil strips, and a dark equation relating to the dark pixel group having the shadow of one of the absorbing foil strips. Even if the shadows of the absorbing foil strips move relative to the arrangement of radiation detecting elements in the radiation detecting device at this time, the shadow of one of the absorbing foil strips exists in one or more pixels of the dark pixel group. Consequently, the object image correcting device can solve the simultaneous equations reliably, to provide a corrected image well suited for diagnosis.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 1 is a functional block diagram illustrating a construction of an X-ray apparatus according to Embodiment 1;

DESCRIPTION OF THE PREFERRED EMBODIMENTS

Figure 2A:
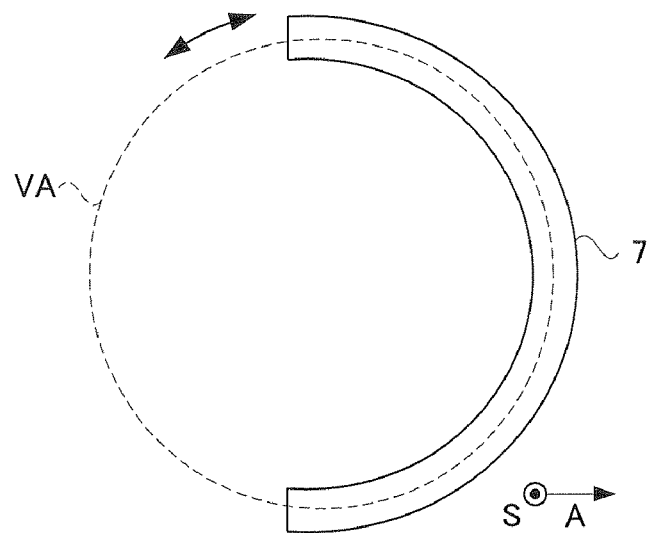
FIG. 2A is a schematic view illustrating rotation of a C-arm according to Embodiment 1.

An embodiment of this invention will be described hereinafter. X-rays in the embodiment correspond to the radiation in this invention.

Embodiment 1

<Construction of X-Ray Apparatus>

As shown in FIG. 1, an X-ray apparatus 1 in Embodiment 1 includes a top board 2 for supporting a patient M, an X-ray tube 3 disposed below the top board 2 for emitting X-rays, a flat panel detector (FPD) 4 disposed above the top board 2 for detecting X-rays, an X-ray tube controller 6 for controlling a tube current and tube voltage of the X-ray tube 3, a C-arm 7 for supporting the X-ray tube 3 and FPD 4, a strut 8 for supporting the C-arm 7, a C-arm moving mechanism 21 for moving the C-arm 7, and a C-arm movement controller 22 for controlling the C-arm moving mechanism 21. The X-ray tube 3 corresponds to the radiation source in this invention. The FPD 4 corresponds to the radiation detecting device in this invention. The C-arm movement controller 22 corresponds to the support movement control device in this invention. The C-arm moving mechanism 21 corresponds to the support moving device in this invention. The C-arm 7 corresponds to the support in this invention.

Figure 2B:
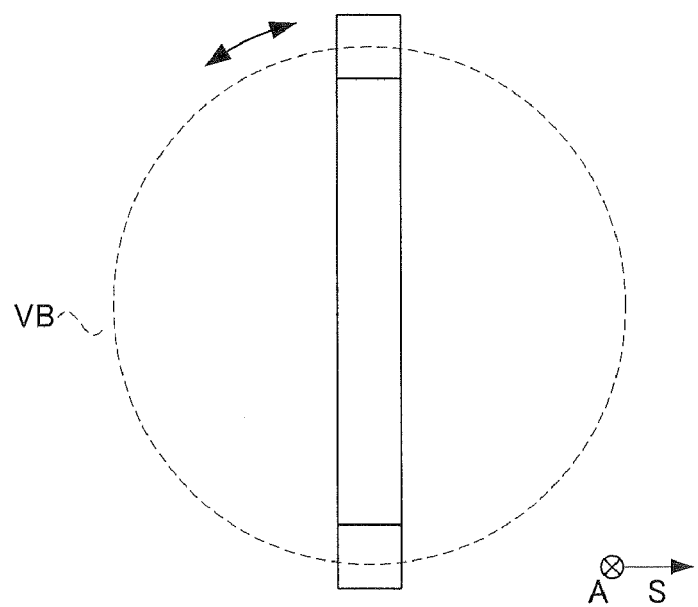
FIG. 2B is a schematic view illustrating rotation of the C-arm according to Embodiment 1.

By the C-arm moving mechanism 21, the C-arm 7 is rotatable as well as movable vertically and horizontally. That is, the C-arm 7 is rotatable along an imaginary circle VA along which the curved C-arm 7 extends as shown in FIG. 2A, and is also rotatable to move opposite ends thereof along an imaginary circle VB on a plane perpendicular to a projecting direction (the direction A along the body axis) in which the opposite ends of the C-arm 7 project as shown in FIG. 2B.

Figure 3:
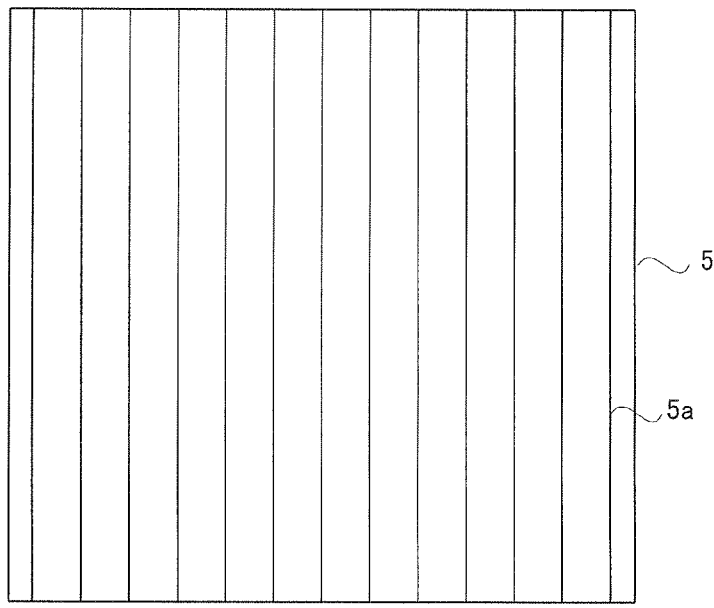
FIG. 3 is a plan view illustrating a construction of an X-ray grid according to Embodiment 1.

An X-ray grid 5 is provided to cover an X-ray detecting surface of the FPD 4. FIG. 3 is a plan view illustrating the construction of the X-ray grid 5 in Embodiment 1. As shown in FIG. 3, the X-ray grid 5 in Embodiment 1 has absorbing foil strips 5a extending longitudinally. The absorbing foil strips 5a are arranged transversely and, when seen as the entire X-ray grid 5, are arranged as in a window blind. The arrangement pitch is 500 µm, for example. The absorbing foil strips 5a are formed of a molybdenum alloy, a tantalum alloy or the like which absorbs X-rays. The X-ray grid 5 corresponds to the radiation grid in this invention.

As shown in FIG. 1, the X-ray apparatus 1 in Embodiment 1 further includes an image generating unit 11 for generating various images, a grid attenuation rate map acquiring unit 12, a separating unit 13, a variation map acquiring unit 14, a variation rate map acquiring unit 15, a patient image correcting unit 16 for generating corrected images from the various images, a console 31 for inputting operator's instructions, a display unit 32 for displaying the correction images, and an information storage unit 33 for storing a variety of information. The patient image correcting unit 16 corresponds to the object image correcting device in this invention.

The X-ray apparatus 1 in Embodiment 1 includes also a main controller 34 for performing an overall control of the components 6, 11, 12, 13, 14, 15, 16 and 22. The main controller 34 has a CPU, and realizes the above components by executing various programs. The above components may be divided into arithmetic units which perform their functions.

Figure 4:
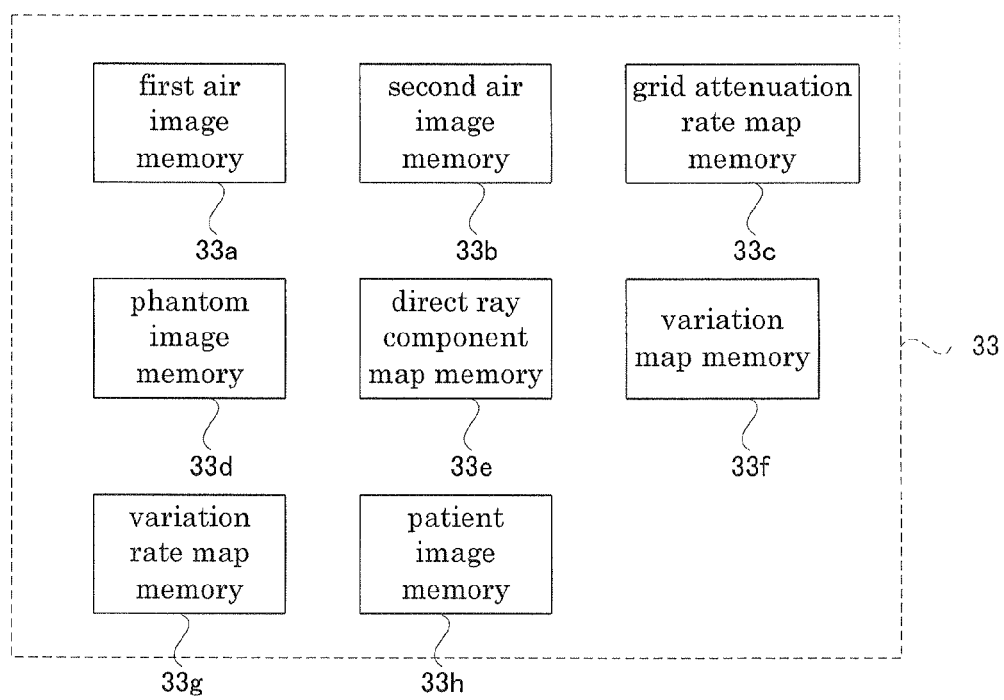
FIG. 4 is a schematic view illustrating a construction of an information storage unit according to Embodiment 1.

As shown in FIG. 4, the information storage unit 33 includes a first air image memory 33a for storing a first air image α, a second air image memory 33b for storing a second air image β, a grid attenuation rate map memory 33c for storing a grid attenuation rate map γ, a phantom image memory 33d for storing a phantom image δ, a direct ray component map memory 33e for storing a direct ray component map ε, a variation map memory 33f for storing a variation map ζ, a variation rate map memory 33g for storing a variation rate map Mη, and a patient image memory 33h for storing patient images ξ. The patient image memory 33h corresponds to the object image storage device in this invention. The phantom image memory 33d corresponds to the phantom image storage device in this invention. The first air image memory 33a and second air image memory 33b correspond to the air image storage device in this invention.

<Operation of the X-Ray Apparatus>

Figure 5:
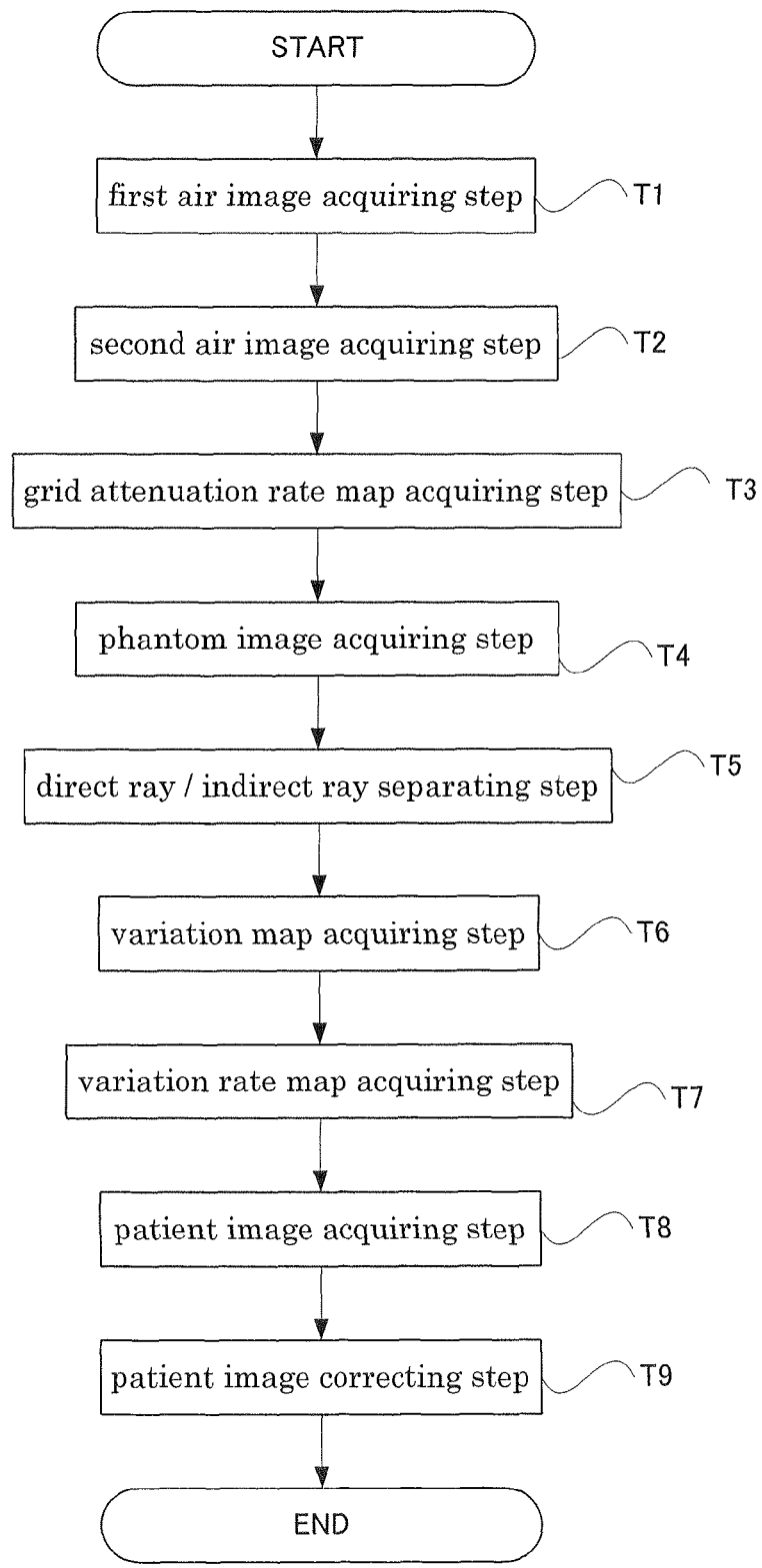
FIG. 5 is a flow chart illustrating operation of the X-ray apparatus according to Embodiment 1.

Operation of the X-ray apparatus 1 will be described next. As shown in FIG. 5, operation of the X-ray apparatus 1 includes a first air image acquiring step T1 for acquiring the first air image α, a second air image acquiring step T2 for acquiring the second air image β, a grid attenuation rate map acquiring step T3 for acquiring the grid attenuation rate map γ from the first air image α and second air image β, a phantom image acquiring step T4 for acquiring the phantom image δ, a direct ray/indirect ray separating step T5 for separating direct ray components and indirect ray components of the phantom image δ using the grid attenuation rate map γ, a variation map acquiring step T6 for acquiring the variation map ζ showing variations in X-ray absorption of the X-ray grid 5 from separated direct ray components, a variation rate map acquiring step T7 for acquiring the variation rate map Mη from the variation map ζ, a patient image acquiring step T8 for acquiring a patient image ξ, and a patient image correcting step T9 for correcting the patient image ξ based on the grid attenuation rate map γ and variation rate map Mη. Each of these steps will be described in chronological order.

<First Air Image Acquiring Step T1>

First, X-raying is carried out with nothing placed on the top board 2 and the X-ray grid 5 not placed on the X-ray detecting surface of the FPD 4. X-rays outputted from the X-ray tube 3 are detected by the FPD 4, and the image generated by the image generating unit 11 at this time is the first air image α. The first air image α shows the intensity of direct X-rays outputted from the X-ray tube 3. This first air image α is stored in the information storage unit 33.

<Second Air Image Acquiring Step T2>

Next, X-raying is carried out with the X-ray grid 5 placed on the X-ray detecting surface of the FPD 4, and without placing anything on the top board 2. The image generated by the image generating unit 11 at this time is the second air image β. This second air image β is stored in the information storage unit 33. The radiography in the first air image acquiring step T1 and second air image acquiring step T2 is the air radiography in this invention.

<Grid Attenuation Rate Map Acquiring Step T3>

The grid attenuation rate map acquiring unit 12 divides each of pixel values in the second air image β by one, corresponding in position, of pixel values in the first air image α. This acquires the grid attenuation rate map γ showing a distribution of grid attenuation rates at the time of direct X-rays passing through the X-ray grid 5. It is thought that indirect X-rays are not produced when the X-rays pass through the X-ray grid 5.

<Phantom Image Acquiring Step T4>

Next, X-raying is carried out with the X-ray grid 5 attached and an acrylic plate placed on the top board 2. This radiography is phantom radiography. The X-rays produce indirect X-rays when passing through the acrylic plate. That is, the phantom image δ generated by the image generating unit 11 at this time includes both direct X-rays and indirect X-rays exiting the acrylic plate. Most of the indirect X-rays generated in the acrylic plate are absorbed by the X-ray grid 5. The indirect X-rays in the phantom image δ are those remaining unabsorbed by the X-ray grid 5. This phantom image δ is stored in the information storage unit 33.

Figure 6A:
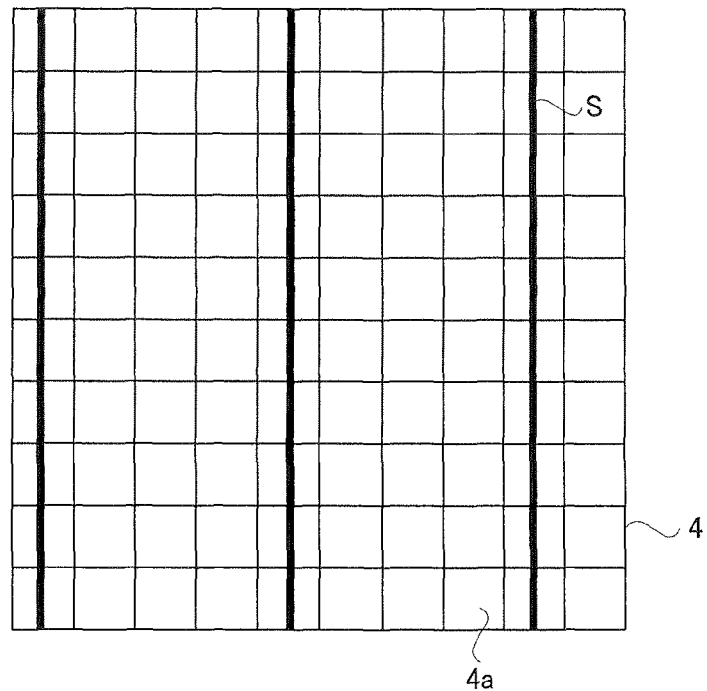
FIG. 6A is a schematic view illustrating operation of the X-ray apparatus according to Embodiment 1.

The phantom image δ acquired at this time will be described further. The absorbing foil strips 5a of the X-ray grid 5 are arranged at intervals of 500 μm in the transverse direction, for example. The FPD 4 has detecting elements 4a arranged at intervals of 125 μm, for example. Consequently, as shown in FIG. 6A, the X-ray detecting surface of the FPD 4 has, regularly arranged in the transverse direction thereon, lines (dark lines) of detecting elements 4a showing shadows S of the absorbing foil strips 5a extending in the longitudinal direction, and lines (light lines) of detecting elements 4a without the shadows S. Specifically, an area of three consecutive light lines and an area of one dark line are arranged alternately in the transverse direction.

Figure 6B:
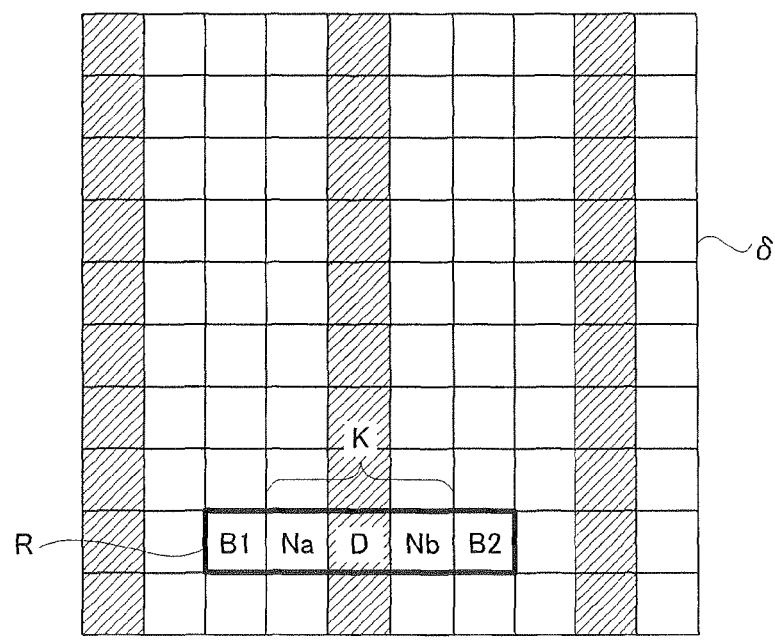
FIG. 6B is a schematic view illustrating operation of the X-ray apparatus according to Embodiment 1.
Figure 7:
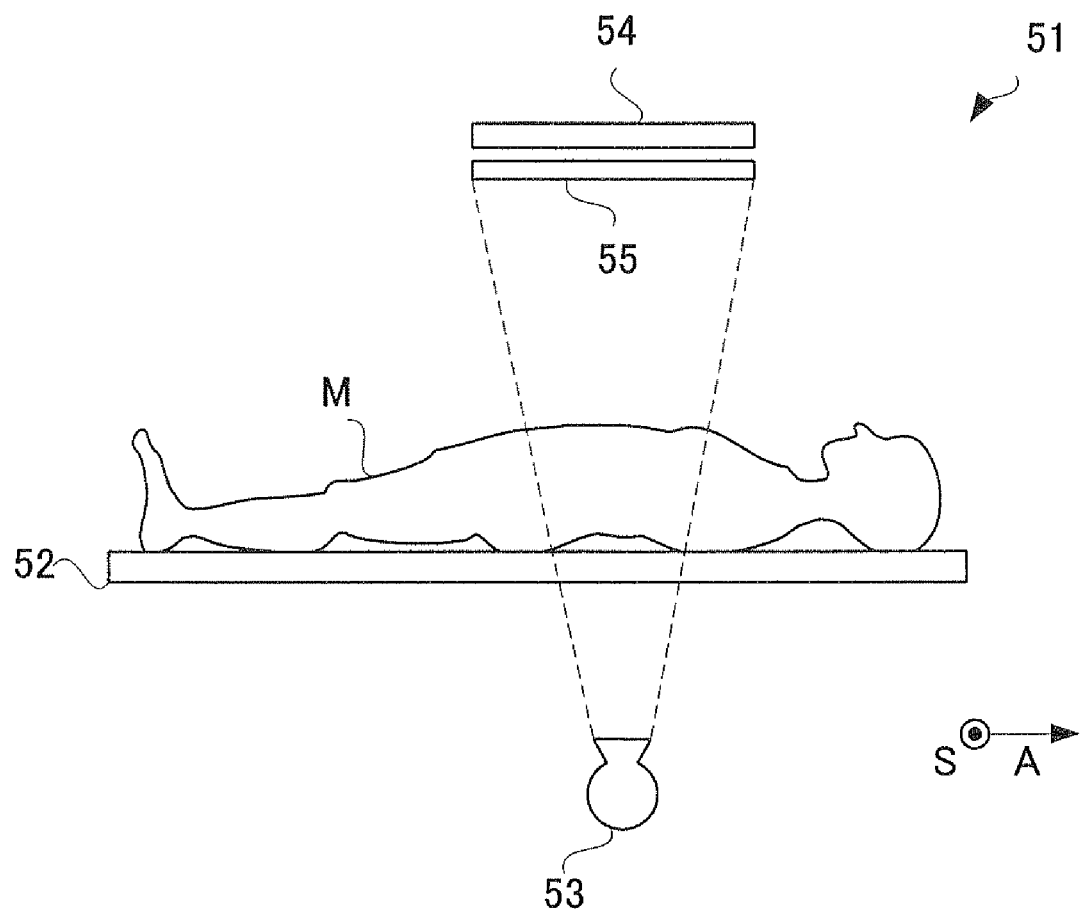
FIG. 7 is a view illustrating a conventional X-ray apparatus.
Figure 8A:
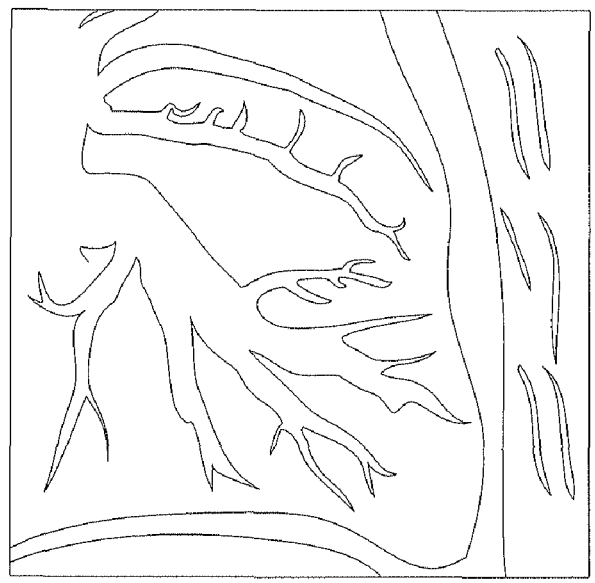
FIG. 8A is a view illustrating the conventional X-ray apparatus.
Figure 8B:
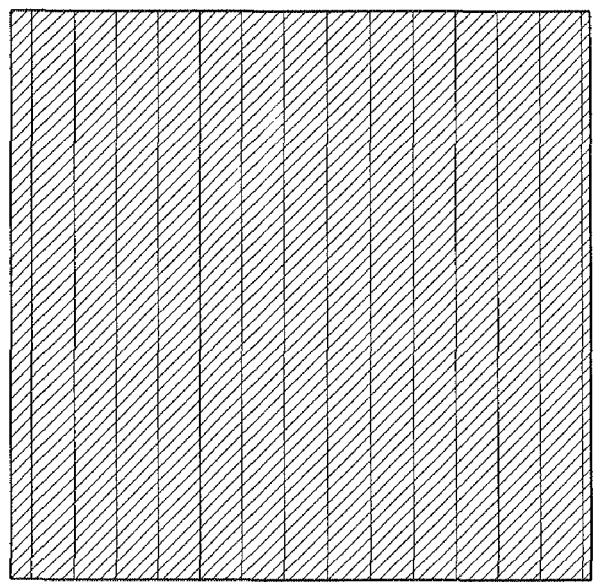
FIG. 8B is a view illustrating the conventional X-ray apparatus.
Figure 9A:
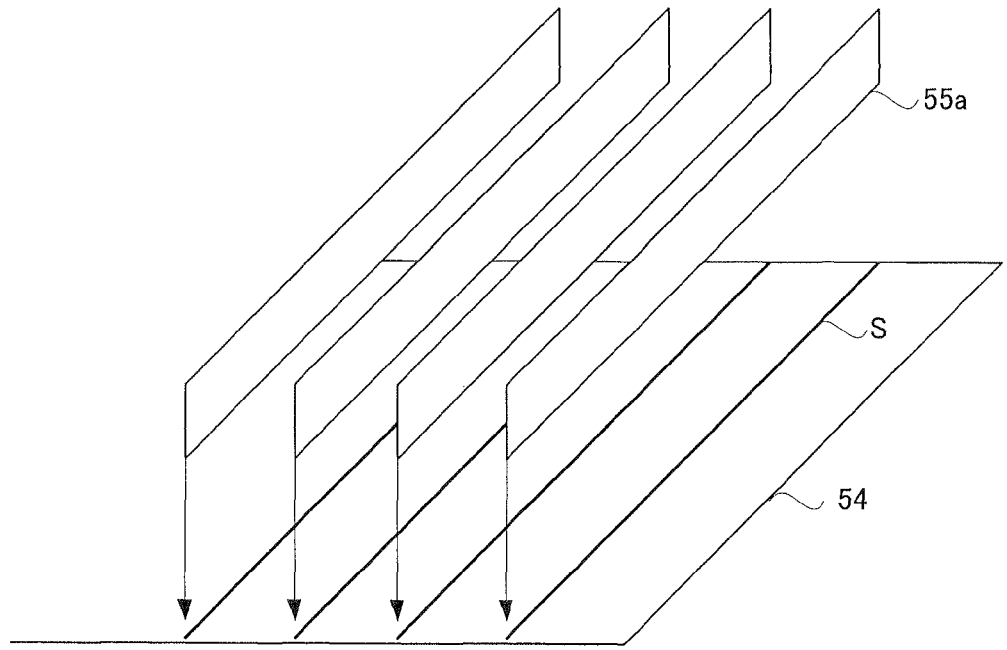
FIG. 9A is a view illustrating the conventional X-ray apparatus.
Figure 9B:
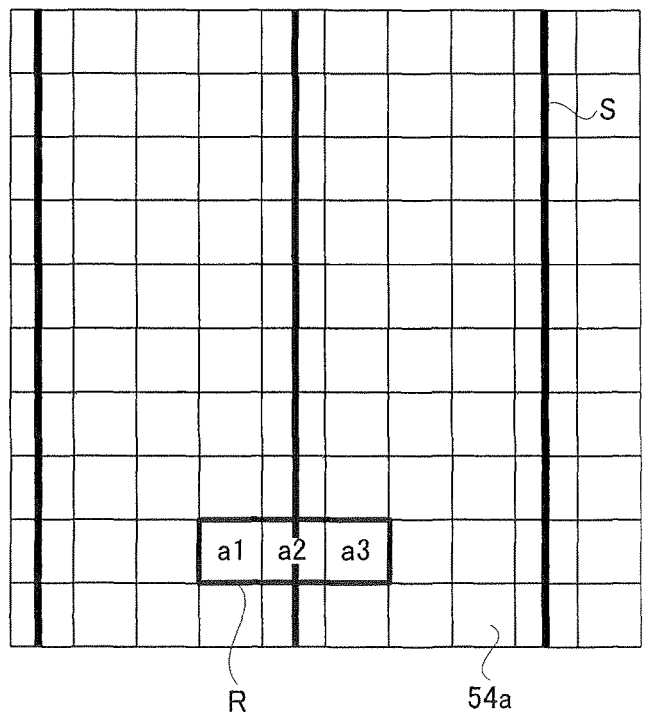
FIG. 9B is a view illustrating the conventional X-ray apparatus.

In the phantom image δ, as shown in FIG. 6B, a dark area with pixel values lowered by one of the absorbing foil strips 5a and a light area not affected by the absorbing foil strips 5a are arranged alternately in the transverse direction. Specifically, an area of three consecutive light lines which are pixel lines free of the shadows S of the absorbing foil strips 5a, and an area of one dark line which is a pixel line showing the shadow S of one of the absorbing foil strips 5a, are arranged alternately in the transverse direction.

<Direct Ray/Indirect Ray Separating Step T5>

Next, the separating unit 13 separates direct ray components from the phantom image δ using the grid attenuation rate map γ. This separation is carried out with reference to five pixels in the phantom image δ. The five pixels here are a pixel group R arranged in the transverse direction as shown in FIG. 6B. The pixel at the middle in the transverse direction is a dark pixel D affected by one of the absorbing foil strips 5a. The two pixels adjoining this dark pixel D in the transverse direction are regarded as adjacent pixels Na and Nb. The dark pixel D and adjacent pixels Na and Nb together constitute a dark pixel group K. The two pixels adjoining this dark pixel group K in the transverse direction are regarded as light pixels B1 and B2.

The pixel value of light pixel B1 includes a direct ray component and an indirect ray component. Assume that $G_1$ is X-ray intensity showing the pixel value of light pixel B1, $\delta P_1$ is the intensity of direct X-rays before transmission through the X-ray grid 5, $C_1$ is a grid attenuation rate (see step T3) for light pixel B1, and $\delta S_1$ is the intensity of indirect X-rays. The direct ray component in light pixel B1 is a product of $\delta P_1$ and $C_1$. Therefore, the following relation is established:

$$G_1 = \delta P_1 \cdot C_1 + \delta S_1 \quad (1)$$

Similarly, where $G_K$ is X-ray intensity of an average of pixel values belonging to the dark pixel group K, and $G_2$ is X-ray intensity showing the pixel value of light pixel B2, there are the following relations:

$$G_K = \delta P_K \cdot C_K + \delta S_K \quad (2)$$

$$G_2 = \delta P_2 \cdot C_2 + \delta S_2 \quad (3)$$

$C_2$ is a grid attenuation rate C for light pixel B2. $C_K$ is an average of grid attenuation rates C for the dark pixel group K. $\delta P_2$ is a direct ray component of light pixel B2. $\delta P_K$ is an average of direct ray components of the dark pixel group K. Here, an approximation $\delta S_K = (\delta S_1 + \delta S_2)/2$ is made. The intensity of direct X-rays exiting the acrylic plate can be regarded as uniform over the entire acrylic plate. Thus, $\delta P_1 = \delta P_K = \delta P_2$. Direct ray components $\delta P_1$, $\delta P_K$ and $\delta P_2$ and indirect ray components $\delta S_1$, $\delta S_K$ and $\delta S_2$ are calculated using the above equations (1), (2) and (3) and approximations thereof. Specifically, these operations can be expressed as follows:

$$\delta P_1 = \delta P_K = \delta P_2 = (G_1 - 2G_K + G_2)/(C_1 - 2C_K + C_2) \quad (4)$$

$$\delta S_1 = G_1 - \delta P_1 \cdot C_1 \quad (5)$$

$$\delta S_K = G_K - \delta P_K \cdot C_K \quad (6)$$

$$\delta S_2 = G_2 - \delta P_2 \cdot C_2 \quad (7)$$

Based on the equations (4)-(7), the separating unit 13 derives a direct ray component and an indirect ray component for each of the dark pixels D appearing in the phantom image δ. Then, the separating unit 13 maps the direct ray components longitudinally and transversely to generate a direct ray component map ε. This direct ray component map ε has an arrangement of direct ray components derived from the dark pixel D and four adjacent pixels. Since the intensity of direct X-rays exiting the acrylic plate can be regarded as uniform over the entire acrylic plate, the direct ray components in the direct ray component map ε should have the same value.

However, variations are found in the value of direct ray components in certain parts of the direct ray component map ε. This is because the arrangement of absorbing foil strips 5a of the X-ray grid 5 is not necessarily ideal. Specifically, since variations occur in transmittance for transmitting indirect ray components through the X-ray grid 5, the phantom image δ cannot fully be divided into direct ray components and indirect ray components, particularly in peripheral regions of the X-ray grid 5. Thus, the variation rate map Mη is generated to show different degrees of indirect ray components being transmitted through different portions of the X-ray grid 5. This variation rate map Mη corresponds to a grid attenuation rate map γ for indirect ray components. That is, the grid attenuation rate map γ shows attenuation rates of the X-ray grid 5 regarding direct ray components, while the variation rate map Mη represents attenuation rates of the X-ray grid 5 regarding indirect ray components.

<Variation Map Acquiring Step T6>

In advance of acquiring the variation rate map Mη, the variation map acquiring unit 14 determines variation components due to the X-ray grid 5 included in phantom image δ. First, an average value $\epsilon_{ave}$ is obtained by averaging direct ray components of portions having minor variations of direct ray components in the direct ray component map ε. The absorbing foil strips 5a of the X-ray grid 5 have such a property that the absorbing foil strips 5a are arranged in a more orderly manner in the central portion than the other portions of the X-ray grid 5. It is assumed that, using this property, the average value Save is obtained by averaging direct ray components of the central portion of the direct ray component map ε. That is, the average value $\epsilon_{ave}$ does not correspond to an average of the entire direct ray component map ε. The variation map acquiring unit 14 uses this average value $\epsilon_{ave}$ to determine variations of indirect ray components in the phantom image δ. When variation ζS of indirect ray components is determined at this time, and the pixel group R present in the phantom image δ consists of light pixels B1 and B2 and dark pixel group K as in FIG. 6B, variation $\zeta S_1$ of indirect ray components for light pixel B1 is expressed as follows:

$$\zeta S_1 = G_1 - \epsilon_{ave} \cdot C_1 \quad (8)$$

Similarly, where $\zeta S_K$ is a variation for dark pixel group K, and $\zeta S_2$ is a variation for light pixel B2, the following equations may be formed:

$$\zeta S_K = G_K - \epsilon_{ave} \cdot C_K \quad (9)$$

$$\zeta S_2 = G_2 - \epsilon_{ave} \cdot C_2 \quad (10)$$

The variation map acquiring unit 14 determines variation $\zeta S$ of indirect ray components for all dark pixels D in the direct ray component map $\epsilon$. The variations $\zeta S_1$, $\zeta S_K$ and $\zeta S_2$ determined are arranged longitudinally and transversely by the variation map acquiring unit 14, thereby generating the variation map $\zeta$.

<Variation Rate Map Acquiring Step T7>

The variation map $\zeta$ is outputted to the variation rate map acquiring unit 15. The variation rate map acquiring unit 15 acquires the average value $\epsilon_{ave}$ of variations $\zeta S$ in the variation map $\zeta$. As noted above, the average value $\epsilon_{ave}$ is not an average of the entire direct ray component map $\epsilon$. The variation rate map acquiring unit 15 divides each of variations $\zeta S$ forming the variation map $\zeta$ by the average value $\epsilon_{ave}$, to generate variation rate map M$\eta$ with variation rates $\eta$ arranged longitudinally and transversely.

The above is a preparatory stage preceding acquisition of a patient image. The subsequent steps will be repeated when acquiring a plurality of patient images. It is sufficient to carry out the above steps T1 through T7 once.

<Patient Image Acquiring Step T8>

Next, X-raying is carried out with the X-ray grid 5 placed on the X-ray detecting surface of the FPD 4, and the patient M placed on the top board 2. The image generated by the image generating unit 11 at this time is a patient image $\xi$ depicting a fluoroscopic image of the patient M. This radiography is patient radiography.

<Patient Image Correcting Step T9>

The patient image $\xi$ is outputted to the patient image correcting unit 16. Based on the grid attenuation rate map $\gamma$ and variation rate map M$\eta$, the patient image correcting unit 16 divides the intensity of X-rays presented by each pixel of the patient image $\xi$ into components of direct X-rays and components of indirect X-rays. The patient image correcting unit 16 determines a direct ray component $\xi P$ for each of the dark pixel D and four pixels adjoining it in the transverse direction in the patient image $\xi$.

Light pixel B1 includes a direct ray component and an indirect ray component. Where $H_1$ is X-ray intensity indicating the pixel value of light pixel B1, and $\xi P_1$ is the intensity of direct X-rays transmitted through the patient M and before passing through the X-ray grid 5, the direct ray component in light pixel B1 is a product of $\xi P_1$ and $C_1$. The intensity of indirect X-rays after passing through the X-ray grid 5 is set to $\rho S_1$.

The intensity of indirect X-rays before passing through the X-ray grid 5 is set to $\xi S_1$. When passing through the X-ray grid 5, indirect X-rays are absorbed with variations by portions of the X-ray grid 5. Indirect ray component $\rho S_1$ in the patient image $\xi$ is the intensity of indirect X-rays after having passed through the X-ray grid 5, which is, so to speak, an apparent component of indirect X-rays. It is not $\xi S_1$ representing the intensity of indirect X-rays before passing through the X-ray grid 5. Between $\rho S_1$ and $\xi S_1$, there is a relation $\rho S_1 = \xi S_1 \cdot \eta_1$. Therefore, the following relation is established:

$$H_1 = \xi P_1 \cdot C_1 + \rho S_1 = \xi P_1 \cdot C_1 + \xi S_1 \cdot \eta_1 \quad (11)$$

Similarly, where $H_K$ is X-ray intensity represented by an average of pixel values belonging to the dark pixel group K, and $H_2$ is X-ray intensity representing the pixel value of light pixel B2, the following equations are formed:

$$H_K = \xi P_K \cdot CK + \rho S_K = \xi P_K \sqrt{C_K} + \xi S_K \cdot \eta_K \quad (12)$$

$$H_2 = \xi P_2 \cdot C_2 + \rho S_2 = \xi P_2 \cdot C_2 + \xi S_2 \cdot \eta_2 \quad (13)$$

$C_2$ is a grid attenuation rate C for light pixel B2, and $C_K$ is an average of grid attenuation rates C for the dark pixel group K. $\xi P_2$ is a direct ray component of light pixel B2, and $\xi P_K$ is an average of direct ray components of the dark pixel group K. $\rho S_2$ and $\xi S_2$ are indirect ray components of light pixel B2, and $\rho S_K$ and $\xi S_K$ are averages of indirect ray components of the dark pixel group K. Here, an approximation $\xi P_K = (\xi P_1 + \xi P_2)/2$ is made. It is generally known that the intensity of indirect X-rays changes gently between adjoining pixels, and therefore an approximation $\xi S_1 = \xi S_K = \xi S_2$ can be made. Direct ray components $\xi P_K$ and $\xi P_2$, and indirect ray components $\xi S_1$, $\xi S_K$ and $\xi S_2$, are calculated using the above equations (11), (12) and (13) and approximations thereof. Specifically, this can be expressed by the following equation:

$$\xi S_1 = \xi S_K = \xi S_2 = (H_1/C_1 - 2H_K/C_K + H_2/C_2)/(\eta_1/C_1 - 2\eta_K/C_K + \eta_2/C_2) \quad (14)$$

In connection with equation (14), the patient image correcting unit 16 once determines indirect ray components of the patient image $\xi$, and based on this, determines direct ray components $\xi P_1$, $\xi P_K$ and $\xi P_2$. In this way, the patient image correcting unit 16 calculates direct ray components $\xi P_1$, $\xi P_K$ and $\xi P_2$ for each dark pixel D of the patient image $\xi$, and obtains a corrected image with only the direct ray components arranged longitudinally and transversely. This corrected image is displayed on the display unit 32 to complete the X-ray fluoroscopy according to Embodiment 1. The above equations (11) and (13) correspond to the light equations in this invention, and the equation (12) corresponds to the dark equation in this invention.

Direct ray components $\xi P_1$, $\xi P_K$ and $\xi P_2$ represent direct X-rays before entering the X-ray grid 5, and therefore the corrected image is free of the striped pattern attributable to the shadows of absorbing foil strips 5a.

As described above, the X-ray apparatus 1 in Embodiment 1 is constructed to acquire a corrected image based on the air images $\alpha$ and $\beta$, phantom image $\delta$ and patient image $\xi$. The corrected image is acquired only from direct X-ray components exiting the patient. This provides a clear X-ray fluoroscopic image with contrast not impaired by indirect X-rays.

Moreover, in acquiring the corrected image, direct X-ray components are obtained by solving simultaneous equations consisting of the light equations relating to light pixels B free of the shadows S of absorbing foil strips 5a, and the dark equation relating to the dark pixel group K having the shadow S of one of the absorbing foil strips 5a. That is, direct X-ray components are obtained on an assumption that the shadow S of one of the absorbing foil strips 5a is present somewhere in the dark pixel group K. Even if the shadows S of absorbing foil strips 5a move relative to the arrangement of X-ray detecting elements 4a in the FPD 4, the shadow S of one of the absorbing foil strips 5a exists in one or more pixels of the dark pixel group K. The shadow S of absorbing foil strip 5a never deviates from the dark pixel group K. Therefore, the patient image correcting unit 16 can solve the simultaneous equations reliably, to provide a corrected image well suited for diagnosis.

The dark pixel group K includes three pixels. The shadows S of absorbing foil strips 5a can move only an amount corresponding to about one pixel transversely of the arrangement of X-ray detecting elements 4a. Therefore, the dark pixel group K can be set to cover three pixels. An excessively large dark pixel group K would lead to a blurred image. According to the above construction, the number of pixels included in the dark pixel group K is a minimum. The patient image correcting unit 16 determines direct X-ray components in the patient image ξ by the three simultaneous equations. Such construction can solve the simultaneous equations reliably.

The X-ray tube 3 and FPD 4 are movable under control of the C-arm movement controller 22. This movement includes rotation. Since the X-ray tube 3 and FPD 4 are heavy objects, the C-arm 7 will bend when rotated. This shifts the positional relationship between X-ray tube 3 and FPD 4 slightly (about 2 mm). Then, the shadows S of absorbing foil strips 5a of the X-ray grid 5 falling on the FPD 4 will move an amount corresponding to about one detecting element transversely of the FPD 4. According to the above construction, even if such a phenomenon occurs, the shadow S of absorbing foil strip 5a will never protrude sideways from the dark pixel group K. Therefore, direct X-ray components of the patient image ξ can be obtained reliably.

This invention is not limited to the foregoing embodiment, but may be modified as follows:

(1) The phantom image acquiring step T4 through the variation rate map acquiring step T7 can be omitted from the foregoing embodiment. As described in the direct ray/indirect ray separating step T5, the grid attenuation rate map γ shows attenuation rates relating to direct ray components of the X-ray grid 5, and the variation rate map Mη shows attenuation rates of indirect ray components of the X-ray grid 5.

While the direct X-rays reflect variations in the grid shape with high accuracy, the indirect X-rays are considerably uniform and show a distribution with very small variations. Therefore, the values of grid attenuation rates $C_1$, $C_K$ and $C_2$ are distributed roughly over 70 to 100%. On the other hand, the values of variation rates $\eta_1$, $\eta_K$ and $\eta_2$ are distributed roughly over 99 to 101%. Thus, the radiography for phantom image 8 can be omitted, and the indirect ray components can be calculated with an error of at most several percents based on $\eta_1=\eta_K=\eta_2=1$. A direct ray image can be obtained by subtracting these indirect ray components from the patient image.

(2) In the foregoing embodiment, the X-ray apparatus 1 includes one C-arm 7, but this invention is not limited to this. This invention may be applied to a biplane system having two C-arms 7.

(3) The foregoing embodiment discusses a medical apparatus. This invention is applicable also to apparatus for industrial use and for the nuclear field.

(4) X-rays used in the foregoing embodiment are an example of radiation in this invention. Therefore, this invention can be adapted also for radiation other than X-rays.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus comprising:
   a radiation source for emitting radiation;
   a radiation detection device having radiation detecting elements arranged longitudinally and transversely for detecting the radiation;
   a radiation grid placed to cover a radiation detecting plane of the radiation detecting device, and having absorbing foil strips extending longitudinally and arranged transversely;
   an image generating device for generating images based on detection signals outputted from the radiation detecting device;
   an air image storage device for storing an air image generated by air radiography carried out without an object under examination interposed between the radiation source and the radiation detecting device;
   an object image storage device for storing an object image generated by object radiography carried out with the object under examination interposed between the radiation source and the radiation detecting device; and
   an object image correcting device for generating a corrected image from components of direct radiation included in the object image and determined based on the air image and the object image;
   wherein the object image correcting device is arranged to generate the corrected image by deriving the components of direct radiation in pixel values of the object image from a dark equation specifying that an average of radiation intensity in a dark pixel group formed of a dark pixel showing a shadow of one of the absorbing foil strips and adjacent pixels transversely adjoining the dark pixel of each image is a sum of the components of direct radiation and components of indirect radiation, and light equations specifying that an average of radiation intensity in light pixels free of the shadows of the absorbing foil strips is a sum of the components of direct radiation and the components of indirect radiation.

2. The radiographic apparatus according to claim 1, further comprising:
   a phantom image storage device for storing a phantom image generated by phantom radiography carried out with a phantom interposed between the radiation source and the radiation detecting device;
   wherein the object image correcting device is arranged to generate the corrected image based on the phantom image in addition to the air image and the object image.

3. The radiographic apparatus according to claim 1, wherein the dark pixel group is formed of three pixels arranged transversely.

4. The radiographic apparatus according to claim 2, wherein the dark pixel group is formed of three pixels arranged transversely.

5. The radiographic apparatus according to claim 1, wherein the object image correcting device is arranged to derive the components of direct radiation in the object image from three simultaneous equations including the dark equation and light equations relating to two light pixels transversely adjoining the dark pixel group.

6. The radiographic apparatus according to claim 2, wherein the object image correcting device is arranged to derive the components of direct radiation in the object image from three simultaneous equations including the dark equation and light equations relating to two light pixels transversely adjoining the dark pixel group.

7. The radiographic apparatus according to claim 3, wherein the object image correcting device is arranged to derive the components of direct radiation in the object image from three simultaneous equations including the dark equation and light equations relating to two light pixels transversely adjoining the dark pixel group.

8. The radiographic apparatus according to claim 4, wherein the object image correcting device is arranged to derive the components of direct radiation in the object image from three simultaneous equations including the dark equation and light equations relating to two light pixels transversely adjoining the dark pixel group.

9. The radiographic apparatus according to claim 1, further comprising:
   a support for supporting the radiation source and the radiation detecting device;
   a support moving device for moving the support; and
   a support movement control device for controlling the support moving device.

10. The radiographic apparatus according to claim 2, further comprising:
    a support for supporting the radiation source and the radiation detecting device;
    a support moving device for moving the support; and
    a support movement control device for controlling the support moving device.

11. The radiographic apparatus according to claim 3, further comprising:
    a support for supporting the radiation source and the radiation detecting device;
    a support moving device for moving the support; and
    a support movement control device for controlling the support moving device.

12. The radiographic apparatus according to claim 4, further comprising:
    a support for supporting the radiation source and the radiation detecting device;
    a support moving device for moving the support; and
    a support movement control device for controlling the support moving device.

13. The radiographic apparatus according to claim 5, further comprising:
    a support for supporting the radiation source and the radiation detecting device;
    a support moving device for moving the support; and
    a support movement control device for controlling the support moving device.

14. The radiographic apparatus according to claim 6, further comprising:
    a support for supporting the radiation source and the radiation detecting device;
    a support moving device for moving the support; and
    a support movement control device for controlling the support moving device.

15. The radiographic apparatus according to claim 7, further comprising:
    a support for supporting the radiation source and the radiation detecting device;
    a support moving device for moving the support; and
    a support movement control device for controlling the support moving device.

16. The radiographic apparatus according to claim 8, further comprising:
    a support for supporting the radiation source and the radiation detecting device;
    a support moving device for moving the support; and
    a support movement control device for controlling the support moving device.

17. The radiographic apparatus according to claim 9, wherein the support comprises a C-arm.

18. The radiographic apparatus according to claim 10, wherein the support comprises a C-arm.

19. The radiographic apparatus according to claim 11, wherein the support comprises a C-arm.

20. The radiographic apparatus according to claim 1, wherein the absorbing foil strips are formed of one of a molybdenum alloy and a tantalum alloy which absorbs radiation.

* * * * *